United States Patent [19]

Heywang et al.

[11] 4,302,466
[45] Nov. 24, 1981

[54] COMBATING PESTS WITH 2,3-DIHYDRO-2,2-DIMETHYL-7-BENZOFURANYL-N-CARBOXYLATED-N-METHYL-CARBAMATES

[75] Inventors: Gerhard Heywang, Bergisch-Gladbach; Alfons Hartmann, Beckingen; Ingeborg Hammann, Cologne; Bernhard Homeyer, Leverkusen, all of Fed. Rep. of Germany

[73] Assignee: Bayer Aktiengesellschaft, Leverkusen, Fed. Rep. of Germany

[21] Appl. No.: 166,262

[22] Filed: Jul. 2, 1980

[30] Foreign Application Priority Data

Jul. 13, 1979 [DE] Fed. Rep. of Germany ....... 2928405

[51] Int. Cl.³ .................... A01N 47/18; C07D 307/86
[52] U.S. Cl. .................... 424/267; 424/246; 424/248.5; 424/251; 424/274; 424/285; 260/326.34; 260/346.73; 544/58.4; 544/58.7; 544/153; 544/376; 546/196
[58] Field of Search ............ 260/346.73, 326.34; 424/285, 246, 248.5, 251, 267, 274; 544/58.4, 58.7, 153, 376; 546/196

[56] References Cited

U.S. PATENT DOCUMENTS 3,857,860 12/1974 Kuhle et al. ............... 260/346.73

FOREIGN PATENT DOCUMENTS 2132936 1/1973 Fed. Rep. of Germany .
1351095 4/1974 United Kingdom .

*Primary Examiner*—Henry R. Jiles
*Assistant Examiner*—Bernard Dentz
*Attorney, Agent, or Firm*—Sprung, Felfe, Horn, Lynch & Kramer

[57] ABSTRACT

2,3-Dihydro-2,2-dimethyl-7-benzofuranyl N-carboxylated-N-methyl-carbamates of the formula

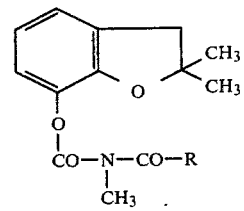

in which R is alkoxy with 1–10 C atoms, alkenoxy or alkynoxy with 5–7 C atoms each optionally substituted by halogen or by a radical of the formula $$-X-R^1 \text{ or } -NR^2R^3; \text{ or } NR^2R^3;$$

X is an oxygen or sulphur atom or a sulphoxide or sulphone group,
$R^1$ is hydrogen or alkyl with 1–4 C atoms,
$R^2$ and $R^3$ independently is hydrogen, alkyl radical with 1–18 C atoms, alkenyl with up to 8 C atoms, or together are $$-(CH_2)_{2-6}-, -CH_2-CH_2-O-CH_2-CH_2-,$$
$$-CH_2-CH-S-CH_2-CH_2-, \text{ or}$$
$$-CH_2-CH_2-\underset{\underset{W}{|}}{N}-CH_2CH_2-, \text{ and}$$

and
W is hydrogen or alkyl wth 1–4 C atoms,
which possess arthropodicidal and nematocidal properties.

12 Claims, No Drawings

COMBATING PESTS WITH 2,3-DIHYDRO-2,2-DIMETHYL-7-BENZOFURANYL-N-CARBOXYLATED-N-METHYL-CARBAMATES

The present invention relates to certain new N-carboxylated N-methyl-carbamates, to a process for their preparation and to their use as agents for combating pests.

It has already been disclosed that certain N-carboxylated N-methylcarbamic acid aryl esters (see DE-OS (German Published Specification) No. 2,132,936) and certain N-chlorocarbonyl-N-methylcarbamic acid aryl esters (see DE-OS (German Published Specification) No. 2,142,496) have insecticidal properties. However, their action frequently leaves something to be desired, especially when low concentrations are applied.

The present invention now provides, as new compounds, the N-carboxylated N-methylcarbamic acid aryl esters of the general formula

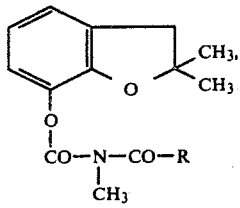

(I)

in which
R represents a straight-chain or branched alkoxy radical with 1–10 C atoms, an alkenoxy or alkynoxy radical with 3–6 C-atoms or a cycloalkoxy radical with 5–7 C atoms, the above radicals being optionally substituted by halogen or by a radical of the general formula $-X-R^1$ or $-YR^2R^3$, or
R represents a radical of the general formula $-YR^2R^3$,
X represents an oxygen or sulphur atom or a sulphoxide or sulphone group,
$R^1$ represents hydrogen or a straight-chain or branched alkyl radical with 1–4 C-atoms,
Y represents nitrogen and
$R^2$ and $R^3$ are the same or different and each represent hydrogen, a branched or straight-chain alkyl radical with 1–18 C-atoms or an alkenyl radical with up to 8 C-atoms, or an alkynyl radical with up to 8 C-atoms, or $Y-R^2R^3$ represents a cyclic amino radical of the general formula

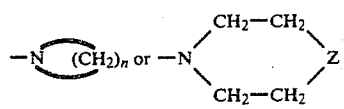

wherein
n represents an integer from 2 to 6 and
Z represents an oxygen or sulphur atom or a nitrogen atom which is substituted by hydrogen or
alkyl, which alkyl substituent on the nitrogen atom can have 1–4 C atoms.

The invention also provides a process for the preparation of a compound of the formula (I) in which 2,2-dimethyl-2,3-dihydrobenzofuran-7-yl N-chlorocarbonyl-N-methyl-carbamate, of the formula

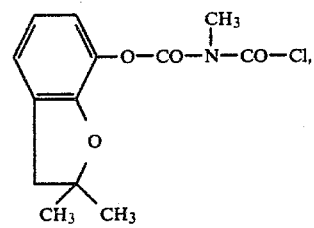

(II)

is reacted with a compound (usually an alcohol or amine) of the general formula

R—H    (III), wherein
R has the meaning indicated above, in the presence of an acid-binding agent and, if appropriate, of a diluent.

It is exceptionally surprising that the compounds according to the invention have a higher insecticidal potency than the above-mentioned N-carboxylated carbamates of the prior art.

Preferred compounds of the formula (I) are those in which R represents $C_{1-4}$-alkoxy, which can be optionally substituted by $C_1$–$C_4$-alkoxy, dialkylamino with 1–4 C-atoms per alkyl radical, $C_1$–$C_4$-alkyl-sulphoxide, $C_1$–$C_4$-alkylthio, $C_{1-4}$-alkyl-sulphone, halogen (especially Cl or F), morpholino, piperidino or OH, or represents mono- or di-alkylamino with 1–18 C atoms per alkyl radical, mono- or di-alkenylamino with 3 to 4 C atoms per alkenyl radical, mono- or dialkynylamino with 3 to 4 C-atoms per alkynyl radical, morpholino, piperidino or $C_{3-4}$-alkynoxy, $C_{3-4}$-alkenoxy or $NH_2$.

In the general formula (III), R furthermore preferably represents an amino radical of the general structure

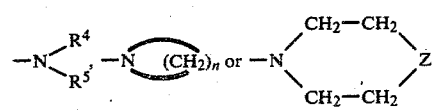

in which
$R^4$ and $R^5$ are identical or different and preferably represent hydrogen, straight-chain or branched alkyl radicals with 1–18 C atoms or straight-chain or branched alkenyl radicals with 3–8 C atoms,
n represents an integer from 2 to 6, and
Z represents an oxygen or sulphur atom or a nitrogen atom which is substituted by hydrogen or alkyl, which alkyl substituent on the nitrogen atom can have 1–4 C atoms. The compounds in which R represents the radicals which are mentioned below as preferred radicals in the case of the compounds of the formula (III) may be mentioned in particular.

The course of the reaction can be represented by the following equation:

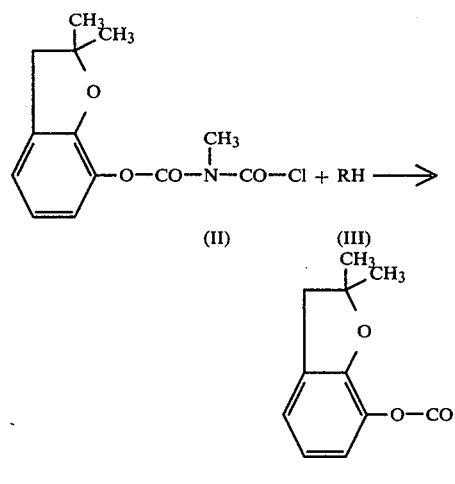

(I)

The starting component (II) can be prepared by the process described in DE-OS (German Published Specification) No. 2,142,496 and can either be isolated in the pure form (melting point: 63° C.), or reacted further, without isolation, in the reaction mixture obtained.

The new compounds wherein R represents the ethylsulphinylethoxy group or the ethylsulphonylethoxy group can also be obtained by a process in which the compound (II) is reacted with ethylthioethanol and then the product is oxidized with hydrogen superoxide or peracid.

Preferred compounds of the formula (III) are those in which R represents methoxy, ethoxy, propargyloxy, allyloxy, cyclohexyloxy, ethylthioethoxy, chloroethoxy, trichloroethoxy, trifluoroethoxy, dimethylaminoethoxy, piperidinoethoxy, morpholinopropoxy, propylsulphinylethoxy, ethylsulphonylethoxy or ethoxyethoxy and isomers thereof.

Preferred compounds of the formula III are furthermore those in which R represents amino, methylamino, dimethylamino, ethylamino, diethylamino, dipropylamino, butylamino, dibutylamino, stearylamino, allylamino, diallylamino, aziridino, pyrrolidino, morpholino, piperidino, piperazino and thiomorpholino groups and isomers thereof.

The compounds of the formula (III) wherein R represents the methoxy, ethoxy, propargyloxy, 2-morpholino-1-methyl-ethoxy, piperidinoethoxy or pyrrolidino-ethoxy group or, especially, the 2-chloroethoxy, 2,2,2-trichloroethoxy, 2,2,2-trifluoroethoxy, 2-dimethyl-amino-ethoxy, 2-ethoxy-ethoxy, 2-ethylthioethoxy, 2-ethylsulphinylethoxy or 2-ethylsulphonylethoxy group, are particularly preferred.

Suitable diluents for the preparative processes according to the invention are any of the inert organic solvents. These include ethers, such as diethyl ether, dioxane or tetrahydrofuran, hydrocarbons, such as benzene or toluene, chlorinated hydrocarbons, such as methylene chloride, chloroform or chlorobenzene, nitriles, esters and ketones, and mixtures of any of these solvents.

Sodium carbonate or, preferably, a tertiary organic base, for example triethylamine or benzyldimethylamine, can be added to the reaction mixture as the acid-binding agent.

The reaction temperature can be varied within a substantial range. In general, the reaction is carried out at between 0° and 100° C., and preferably at from 10° to 60° C.

The reactants are usually employed in equimolar amounts. In some cases, it is advantageous to employ components (II) and (III) in the molar ratio 1:5, preferably 1:3.

The active compounds are well tolerated by plants, have a favorable level of toxicity to warm-blooded animals, and can be used for combating arthropod pests, especially insects and acarids, and nematode pests which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and *Scutigera spec.;* from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus, Gryllotalpa* spp., *Locusta migratoria migratorioides, Melanoplus differentialis* and *Schistocerca gregaria;* from the order of the Dermaptera, for example *Forficula auricularia;* from the order of the Isoptera, for example *Reticulitermes* spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae, Myzus* spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudococcus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Tricho-*

*plusia ni, Carpocapsa pomonella,* Pieris spp., Chilo spp., *Pyrausta nubilalis, Ephestia kuehniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamensis,* Anthonomus spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., Monomorium pharaonis and Vespa spp;

from the order of the Diptera, for example Aedes spp., Anopheles spp.; Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp.;

from the class of the Arachnida, for example *Scorpio maurus* and *Latrodectus mactans;* from the order of the Acarina, for example Acarus siro, Argas spp., Ornithodoros spp., *Dermanyssus gallinae, Eriophyes ribis, Phyllocoptruta oleivora,* Boophilus spp., Rhipicephalus spp., Amblyomma spp., Hyalomma spp., Ixodes spp., Psoroptes spp., Chorioptes spp., Sarcoptes spp., Tarsonemus spp., *Bryobia praetiosa,* Panonychus spp. and Tetranychus spp.

The plant-parasitic nematodes include Pratylenchus spp., *Radopholus similis, Ditylenchus dipsaci, Tylenchulus semipenetrans,* Heterodera spp.; Meloidogyne spp.; Aphelenchoides spp., Longidorus spp., Xiphinema spp., and Trichodorus spp.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol esters, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

When used against pests harmful to health and pests of stored products, the active compounds are distinguished by an excellent residual activity on wood and clay as well as a good stability to alkali on limed substrates.

The active compounds according to the invention are also suitable for combating ectoparasites and endoparasites in the field of veterinary medicine.

In the veterinary field, the active compounds according to the invention may be used in a known manner, such as orally in the form of, for example, tablets, capsules, drenches and granules; dermally by means of, for example, dipping, spraying, pouring-on, spotting-on and powdering; and parenterally, for example by means of injections.

The present invention also provides a pesticidal composition containing as active ingredient a compound of the present invention in admixture with a solid or liquefied gaseous diluent or carrier or in admixture with a liquid diluent or carrier containing a surface-active agent.

The present invention also provides a method of combating pests (in particular anthropods, especially insects or acarids, or nematodes) which comprises applying to the pests, or to a habitat thereof, a compound of the present invention alone or in the form of a composition containing as active ingredient a compound of the present invention in admixture with a diluent or carrier.

The present invention also provides a method of freeing or protecting domesticated animals from parasites which comprises applying to said animals a compound according to the present invention, in admixture with a diluent or carrier.

The present invention further provides crops protected from damage by pests by being grown in areas in which immediately prior to and/or during the time of the growing a compound of the present invention was applied alone or in admixture with a diluent or carrier.

It will be seen that the usual methods of providing a harvested crop may be improved by the present invention.

The present invention further provides domesticated animals whenever freed or protected from parasites by the application to said animals of a compound according to the present invention, in admixture with a diluent or carrier.

PREPARATIVE EXAMPLES

EXAMPLE 1

(a) The starting compound (II) could be prepared as follows:

40.4 g (0.4 mol) of triethylamine were added dropwise to a solution of 65.6 g (0.4 mol) of 2,2-dimethyl-2,3-dihydrobenzofuran-7-ol and 62.4 g (0.4 mol) of N-bis-chlorocarbonyl-methylamine in 1.2 liters of toluene, while stirring. The mixture was stirred at room temperature for 8 hours, the amine hydrochloride which had precipitated was filtered off and the filtrate was evaporated in vacuo. After a short time, the residue crystallized. It was stirred with petroleum ether and filtered off. Yield: 113.4 g of colorless crystals of melting point 63° C.

(b) 2,3-Dihydro-2,2-dimethyl-7-benzofuranyl N-[2-(N',N'-dimethylamino)ethoxycarbonyl]-N-methyl-carbamate.

7 g (0.025 mol) of the chlorocarbonyl compound (II) and 2.2 g (0.025 mol) of dimethylaminoethanol were stirred with 2.1 g of sodium bicarbonate in 60 ml of toluene for 2 days. The filtered solution was washed with water and the organic phase was dried over sodium sulphate and concentrated in vacuo. Last residues of solvent were removed under a high vacuum at 40° C. Yield: 7.8 g of a colorless oil (92% of theory) of $n_D^{20} = 1.5120$.

EXAMPLE 2

2,3-Dihydro-2,2-dimethyl-7-benzofuranyl N-ethoxycarbonyl-N-methyl-carbamate 4 ml of triethylamine were added dropwise to 7 g (0.025 mole) of the chlorocarbonyl compound (II) and 1.2 g of ethanol in 100 ml of toluene or 100 ml of methylene chloride at room temperature. When the addition had ended, the mixture was stirred for a further hour. It was worked up as in Example 1.

Yield: 5.4 g of a colorless oil (73% of theory) of $n_D^{20} = 1.5165$.

EXAMPLE 3 (Compound 7)

2,3-Dihydro-2,2-dimethyl-7-benzofuranyl N-(2-ethylsulphinylethoxycarbonyl)-N-methyl-carbamate 2.7 ml of 40% strength hydrogen superoxide were added dropwise to 10.6 g (0.03 mol) of 2,3-dihydro-2,2-dimethyl-7-benzofuranyl N-(2-ethylthioethoxycarbonyl)-N-methyl-carbamate in 40 ml of glacial acetic acid at 0° C. The next day, the mixture was poured into 300 ml of water and extracted with methylene chloride. The solution was neutralized with sodium bicarbonate. After filtration, the organic phase was worked up as described in Example 1. Yield: 11 g of a colorless oil (98% of theory) of $n_D^{20} = 1.5320$.

EXAMPLE 4 (Compound 23)

2,3-Dihydro-2,2-dimethyl-7-benzofuranyl N-piperidinocarbonyl-N-methyl-carbamate 5.7 g (0.02 mol) of the chlorocarbonyl compound (II) were dissolved in 50 ml of methylene chloride, 4 ml (0.04 mol) of piperidine were added dropwise and the mixture was then stirred for a further hour. After adding 100 ml of water, the organic phase was separated off and dried over sodium sulphate. After concentrating the solution, the product was crystallized by adding petroleum ether. Yield: 5 g of colorless crystals (73% of theory) of melting point 98°–100° C.

TABLE

Summary of the new insecticides

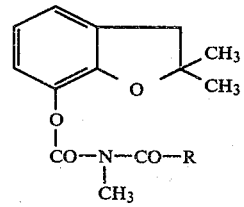

(I)

| Compound No. | R | $n_D^{20}$ | Melting point °C. |
|---|---|---|---|
| 1 | O—CH$_2$—CH$_2$—N(CH$_3$)(CH$_3$) | 1.5120 | |
| 2 | OCH$_2$—CH$_3$ | 1.5165 | |
| 3 | OCH$_3$ | 1.5242 | |
| 4 | O—CH$_2$—C≡CH | | 90° |
| 5 | O—CH$_2$—CH$_2$—S—CH$_2$—CH$_3$ | 1.5293 | |
| 6 | O—CH$_2$—CH$_2$—O—CH$_2$—CH$_3$ | 1.5133 | |
| 7 | O—CH$_2$—CH$_2$—SO—CH$_2$—CH$_3$ | 1.5320 | |
| 8 | O—CH$_2$—CH$_2$—SO$_2$—CH$_2$—CH$_3$ | 1.5260 | |

TABLE-continued
Summary of the new insecticides (I)

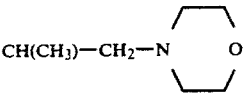

| Compound No. | R | $n_D^{20}$ | Melting point °C. |
|---|---|---|---|
| 9 | O—CH₂—CH₂—Cl | 1.5282 | |
| 10 | O—CH₂—CH₃ | 1.4871 | |
| 11 | O—CH₂CCl₃ | 1.5272 | |
| 12 | O—CH(CH₃)—CH₂—N(morpholino) | 1.5218 | |
| 13 | O—CH₂—CH₂—N(morpholino) | 1.5180 | |
| 14 | O—CH₂—CH₂—N(piperidino) | 1.5258 | |
| 15 | O—CH₂—CH₂—OH | 1.5283 | |
| 16 | NHCH₃ | | 95–97 |
| 17 | N(C₂H₅)₂ | 1.5159 | |
| 18 | N(iC₃H₇)₂ | | 126 |
| 19 | NH—CH₂—CH(CH₃)₂ | | 80 |
| 20 | NH—C₁₈—H₃₇ | | 50* |
| 21 | N(CH₂—CH=CH₂)₂ | 1.5258 | |
| 22 | N(morpholino) | | 113 |
| 23 | N(morpholino) | | 98–100 |
| 24 | NH₂ | | 136–138 |

The pesticidal activity of the compounds of this invention is illustrated by the following examples wherein the compounds according to the present invention are each identified by the number (given in brackets) from the table hereinabove:

EXAMPLE 5

Myzus test
Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (Brassica oleracea) which has been heavily infested with peach aphids (Myzus persicae) were treated by being dipped into the preparation of active compound of the desired concentration.

After the specified periods of time, the degree of destruction was determined as a percentage; 100% meant that all of the aphids were killed whereas 0% meant that none of the aphids were killed.

In this test, for example, the following compounds showed a superior activity compared with the prior art: (3), (2), (4), (23), (11), (12), (9), (1), (14), (7) and (8).

EXAMPLE 6

Doralis test (systemic action)
Solvent: 3 parts by weight of dimethylformamide
Emulsifier: 1 part by weight of alkylaryl polyglycol ether To produce a suitable preparation of active compound, 1 part by weight of active compound was mixed with the stated amount of solvent and the stated amount of emulsifier, and the concentrate was diluted with water to the desired concentration.

Bean plants (Vicia faba) which had been heavily infested with the bean aphid (Doralis fabae) were each watered with 20 ml of the preparation of the active compound of the desired concentration in such a way that the preparation of the active compound penetrated into the soil without wetting the shoot. The active compound was taken up by the roots and passed to the shoot.

After the specified periods of time, the destruction in % was determined. 100% meant that all the aphids had been killed; 0% meant that none of the aphids had been killed.

In this test, for example, the following compounds showed a superior activity compared with the prior art: (3), (2), (4), (23), (11), (12), (9), (1), (14) and (8).

EXAMPLE 7

Test insect: Phaedon cochleariae larvae
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (Brassica oleracea). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

In this test, for example, the following compounds showed a superior action compared with the prior art: (7) and (8).

EXAMPLE 8

Test insect: Myzus persicae
Solvent: 3 parts by weight of acetone

Emulsifier: 1 part by weight of alkylaryl polyglycol ether

To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test insects after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

In this test, for example, the following compounds showed a superior action compared with the prior art: (4), (7) and (9).

EXAMPLE 9

Test insect: *Phorbia antiqua* grubs in the soil
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was pracitically immaterial, the only decisive factor being the amount by weight of active compound per unit volume of soil, which is quoted hereinafter in ppm (=mg/l). The treated soil was filled into pots and the pots were left to stand at room temperature.

After 24 hours the test insects were introduced into the treated soil and after a further 2 to 7 days the degree of effectiveness of the active compound was determined in % by counting the dead and the live test insects. The degree of effectiveness was 100% if all of the test insects had been killed and was 0% if exactly as many test insects were still alive as in the case of the untreated control.

In this test, for example, the following compounds showed a superior action compared with the prior art: (9), (11), (12) and (23).

EXAMPLE 10

Test nematode: *Meloidogyne incognita*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with soil which was heavily infested with the test nematodes. The concentration of the active compound in the preparation was of practically no importance; only the amount of active compound per unit volume of soil, which is given hereinafter in ppm (=mg/l), was decisive. The treated soil was filled into pots, lettuce was sown in and the pots were kept at a greenhouse temperature of 27 degrees C.

After 4 weeks, the lettuce roots were examined for infestation with nematodes (root galls), and the degree of effectiveness of the active compound was determined as a percentage. The degree of effectiveness was 100% when infestation was completely avoided; it was 0% when the infestation was exactly the same as in the case of the control plants in untreated soil which had been infested in the same manner.

In this test, for example, the following compound showed a superior activity compared with the prior art: (9).

It will be appreciated that the instant specification and examples are set forth by way of illustration and not limitation, and that various modifications and changes may be made without departing from the spirit and scope of the present invention.

What is claimed is:

1. A 2,3-dihydro-2,2-dimethyl-2-benzofuranyl N-carboxylated-N-methyl carbamate of the formula

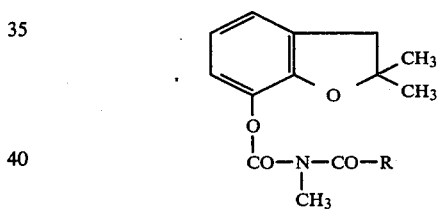

in which
R is alkenoxy or alkynoxy with 3–6 C atoms or a cycloalkoxy radical with 5–7 C atoms each optionally substituted by halogen or by a radical of the formula $$-X-R^1 \text{ or } -NR^2R^3;$$

X is an oxygen or sulphur atom or a sulphoxide or sulphone group,
$R^1$ is hydrogen or alkyl with 1–4 C atoms,
$R^2$ and $R^3$ independently is hydrogen, alkyl radical with 1–18 C atoms, alkenyl with up to 8 C atoms, or together are $$-(CH_2)_{2-6}-, -CH_2-CH_2-O-CH_2-CH_2-,$$
$$-CH_2-CH_2-S-CH_2-CH_2-, \text{ or}$$
$$-CH_2-CH_2-\underset{\underset{W}{|}}{N}-CH_2-CH_2-, \text{ and}$$

and
W is hydrogen or alkyl with 1–4 C atoms.

2. A 2,3-dihydro-2,2-dimethyl-2-benzofuranyl N-carboxylated-N-methyl carbamate of the formula

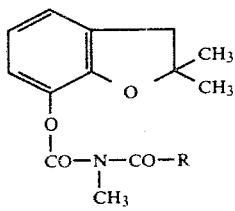

in which

R is alkoxy with 1–10 C atoms substituted by halogen or by a radical of the formula —X—R$^1$ or —NR$^2$R$^3$;

X is an oxygen or sulphur atom or a sulphoxide or sulphone group,

R$^1$ is hydrogen or alkyl with 1–4 C atoms,

R$^2$ and R$^3$ independently is hydrogen, alkyl radical with 1–18 C atoms, alkenyl with up to 8 C atoms, or together are

—(CH$_2$)$_{2-6}$—, —CH$_2$—CH$_2$—O—CH$_2$—CH$_2$—,

—CH$_2$—CH$_2$—S—CH$_2$—CH$_2$—, or

—CH$_2$—CH$_2$—N(W)—CH$_2$—CH$_2$—, and and

W is hydrogen or alkyl with 1–4 C atoms.

3. A compound according to claim 2, in which R is C$_{1-4}$-alkoxy substituted by C$_{1-4}$-alkoxy, dialkylamino with 1–4 C atoms per alkyl radical, C$_{1-4}$-alkyl-sulphoxide, C$_{1-4}$-alkylthio, C$_{1-4}$-alkylsulphone, halogen, morpholino, piperidino or OH.

4. A compound according to claim 2, wherein such compound is 2,3-dihydro-2,2-dimethyl-7-benzofuranyl N-[2-(N',N'-dimethylamino)ethoxycarbonyl]-N-methyl-carbamate of the formula

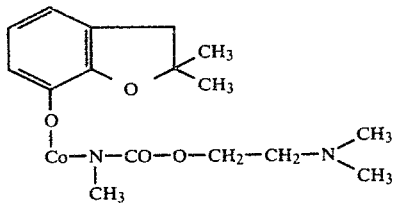

5. A compound according to claim 2, wherein such compound is 2,3-dihydro-2,2-dimethyl-7-benzofuranyl N-(2-chloroethoxycarbonyl)-N-methyl-carbamate of the formula

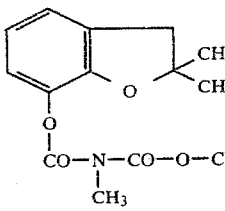

6. A compound according to claim 2, wherein such compound is 2,3-dihydro-2,2-dimethyl-7-benzofuranyl N-(2-trichloroethoxycarbonyl)-N-methyl-carbamate of the formula

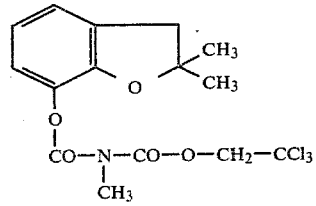

7. A compound according to claim 2, wherein such compound is 2,3-dihydro-2,2-dimethyl-7-benzofuranyl N-[2-(piperidin-1-yl)ethoxycarbonyl]-N-methyl-carbamate of the formula

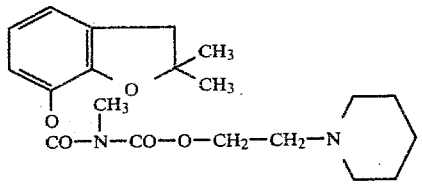

8. An arthropodicidal and nematocidal composition comprising an arthropodicidally or nematocidally effective amount of a compound according to claim 1 in admixture with a diluent.

9. A method of combating arthropods and nematodes which comprises applying to the arthropods and nematodes, or to a habitat thereof, an arthropodicidally or nematocidally effective amount of a compound according to claim 1.

10. An arthropodicidal and nematocidal composition comprising an arthropodicidally or nematocidally effective amount of a compound according to claim 2 in admixture with a diluent.

11. A method of combating arthropods and nematodes which comprises applying to the arthropods and nematodes, or to a habitat thereof, an arthropodicidally or nematocidally effective amount of a compound according to claim 2.

12. The method according to claim 11, wherein said compound is
2,3-dihydro-2,2-dimethyl-7-benzofuranyl N-[2-(N',N'-dimethylamino)ethoxycarbonyl]-N-methyl-carbamate,
2,3-dihydro-2,2-dimethyl-7-benzofuranyl N-(2-chloroethoxycarbonyl)-N-methyl-carbamate,
2,3-dihydro-2,2-dimethyl-7-benzofuranyl N-(2-trichloroethoxycarbonyl)-N-methyl-carbamate or
2,3-dihydro-2,2-dimethyl-7-benzofuranyl N-[2-piperidin-1-yl)-ethoxycarbonyl]-N-methyl-carbamate,
and is applied to domesticated animals to protect them from parasites.

* * * * *